United States Patent
Ohkoshi et al.

(10) Patent No.: US 6,500,347 B2
(45) Date of Patent: Dec. 31, 2002

(54) PROCESS FOR RECOVERING CRYSTALS FROM A SLURRY

(75) Inventors: Fumio Ohkoshi, Okayama-ken (JP); Masato Inari, Okayama-ken (JP)

(73) Assignees: Mitsubishi GAs Chemical Company, Inc., Tokyo (JP); Toyo Boseki Kabushiki Kaisha, Osaka (JP); Mizushima Aroma Company, Ltd., Kurashiki (JP)

( * ) Notice: Subject to any disclaimer, the term of this patent is extended or adjusted under 35 U.S.C. 154(b) by 0 days.

(21) Appl. No.: 09/897,610

(22) Filed: Jul. 3, 2001

(65) Prior Publication Data

US 2002/0003117 A1 Jan. 10, 2002

(30) Foreign Application Priority Data

Jul. 5, 2000 (JP) .......................................... 2000-203772

(51) Int. Cl.[7] .......................... B01D 37/00; B01D 33/073
(52) U.S. Cl. ...................... 210/772; 210/784; 210/791; 210/805; 210/391; 210/402; 210/411; 562/412; 562/413; 562/414
(58) Field of Search ................................ 210/772, 784, 210/791, 805, 391, 402, 407, 408, 409, 411; 562/412, 413, 414

(56) References Cited

U.S. PATENT DOCUMENTS

| | | | | |
|---|---|---|---|---|
| 5,093,001 A | * | 3/1992 | Veda | 210/403 |
| 5,470,473 A | * | 11/1995 | Park et al. | 210/402 |
| 5,589,079 A | * | 12/1996 | Park et al. | 210/784 |
| 5,676,847 A | * | 10/1997 | Yamamoto et al. | 210/784 |

* cited by examiner

*Primary Examiner*—Robert J. Popovics
(74) *Attorney, Agent, or Firm*—Antonelli, Terry, Stout & Kraus, LLP

(57) ABSTRACT

A process for recovering crystals from a slurry which comprises supplying a slurry comprising crystals and a solvent to a rotary vacuum filter and successively conducting filtration under suction, washing, filtration under suction and cleavage of a cake continuously by rotation of a cylindrical filter medium, wherein a vapor having a same composition as that of the solvent is supplied as a blowing gas for cleaving the cake.

The crystals can be continuously recovered for a long period of time without clogging of a filter medium when the crystals are recovered from a slurry by using a rotary vacuum filter.

4 Claims, 2 Drawing Sheets

PROCESS FOR RECOVERING CRYSTALS FROM A SLURRY

BACKGROUND OF THE INVENTION

1. Field of the Invention

The present invention relates to a process for recovering crystals from a slurry which is used in processes for producing various organic chemical products such as a process for producing terephthalic acid by liquid phase oxidation of para-xylene.

2. Description of the Prior Art

When terephthalic acid is produced by liquid phase oxidation of para-xylene, formed terephthalic acid is crystallized in the mother liquor and a slurry containing crystals of terephthalic acid is formed. Crude terephthalic acid is obtained by recovering the crystals from the slurry. When the obtained crude terephthalic acid is dissolved and purified by treatments for purification such as oxidation treatments and reduction treatments and the purified terephthalic acid is crystallized, a slurry containing crystals can be obtained.

In both treatments of a slurry described above, a rotary vacuum filter (referred to as RVF hereinafter) which run successive filtration under suction, washing, filtration under suction and cleavage of a cake in a batch operation using is most frequently conducted as the process for recovering the crystals from the slurry.

In the operation of RVF, filtration under suction, washing, filtration under suction and cleavage of a cake are conducted successively while a cylindrical filter medium is rotated. However, a continuous operation for a long period of time is difficult in the operation of RVF since the filter medium is clogged during the continuous operation.

SUMMARY OF THE INVENTION

The present invention has an object of proposing a process which enables recovery of crystals continuously for a long period of time without clogging of a filter medium when the crystals are recovered from a slurry by using RVF.

As the result of intensive studies by the present inventors on RVF having the above problem, it was found that cleavage of a cake can be facilitated by supplying a vapor having the same composition as that of a solvent as the blowing gas used for cleavage of the cake in the step of cleavage by RVF and the operation of RVF can be continued for a long period of time. The present invention has been completed based on the knowledge.

The present invention provides a process for recovering crystals from a slurry which comprises supplying a slurry comprising crystals and a solvent to a rotary vacuum filter and successively conducting filtration under suction, washing, filtration under suction and cleavage of a cake continuously by rotation of a cylindrical filter medium, wherein a vapor having a same composition as that of the solvent is supplied as a blowing gas for cleaving the cake.

The numbers in the Figures have the following meanings: 1: RVF (a rotary vacuum filter); 2: a casing; 3: a filter medium; 4: a slurry; 5: a filtering area; 6: a filtrate; 7: a gas; 8: a portion for suction; 9: a cake; 10: a pipe for a washing liquid; 11: an area for washing; 12: an area for removing a liquid; 13: a portion for collecting a liquid; 14: a portion for blowing; 15; a sealing portion; 16: an area for cleavage; 17: a pipe for ; supplying a blowing gas; 18: a portion for supplying a slurry; 19: a dam; 20: a portion for circulating a slurry; 21: a portion for taking out a cake; 22: a tank for a slurry; 23: a pump; 24: a pump; 25: a tank for a filtrate; 26: a pump; 27: a cooler; 28: a mist separator; 29: a vacuum pump; 30: a separator sealed with a liquid; 31: a mist separator; 32: a line for supplying the vapor of a solvent; 33: a shutter; 34: a shutter; 35: a drier; and 36: an outlet for a product.

DETAILED DESCRIPTION OF THE INVENTION

The process of the present invention will be described in detail in the following with reference to the Figures.

Figure 1:
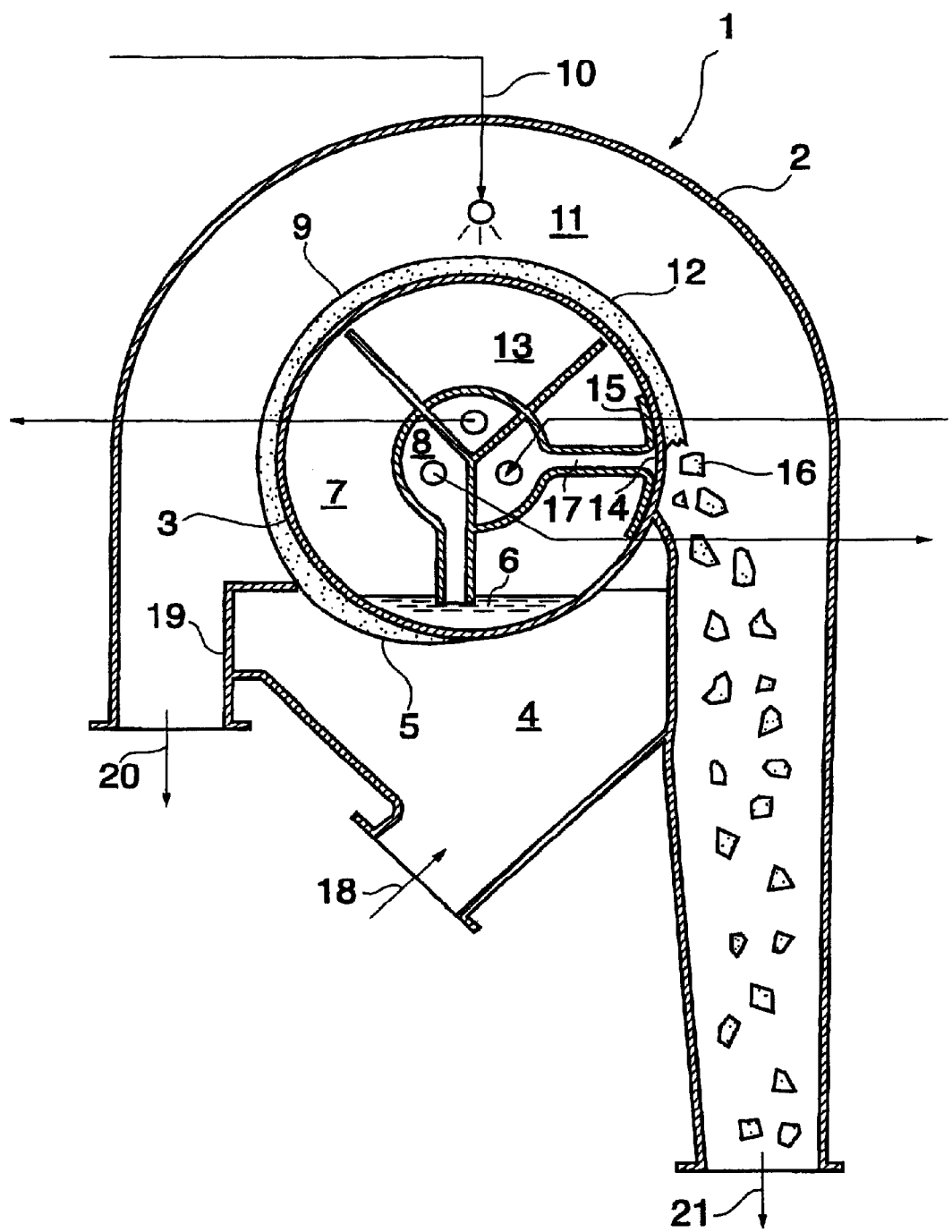
FIG. 1 shows a sectional view of RVF.

In the sectional view shown in FIG. 1, a filter medium 3 having a horizontal cylindrical shape is disposed in a casing 2 of RVF 1 in a manner such that the filter medium 3 can be rotated. A lower portion of the filter medium 3 is dipped into a slurry 4 kept at a lower portion of the casing 2 and form a filtering area 5. At the inside of the filtering area 5, a portion for suction 8 into which a filtrate 6 and a blowing gas 7 are sucked is formed.

At an upper portion of the filter medium 3, a pair of pipes for a washing liquid 10 used for washing a cake 9 are disposed in a manner such that the pipes are faced to each other. At suitable positions relative to those of the pipes for a washing liquid 10, an area for washing 11 and an area for removing a liquid 12 are formed on the filter medium 3 and a portion for collecting a liquid 13 into which the liquid is collected is formed at the inside of these areas.

At the inside of the filter medium 3, a portion for blowing 14 used for cleavage of a cake 9 and a sealing portion 15 are disposed. The corresponding portion of the filter medium 3 is an area for cleavage 16. At the inside of the area for cleavage 16, a pipe for supplying blowing gas 17 which supplies a blowing gas obtained by mixing a non-condensing gas such as nitrogen gas with the vapor of a solvent is connected.

The slurry to be treated by RVF 1 is supplied via a portion for supplying a slurry 18. A dam 19 is disposed so that the surface position of the slurry is maintained. The slurry overflowing the dam 19 is discharged from a portion for circulating a slurry 20 and a cake is discharged from an outlet for a cake 21.

Figure 2:
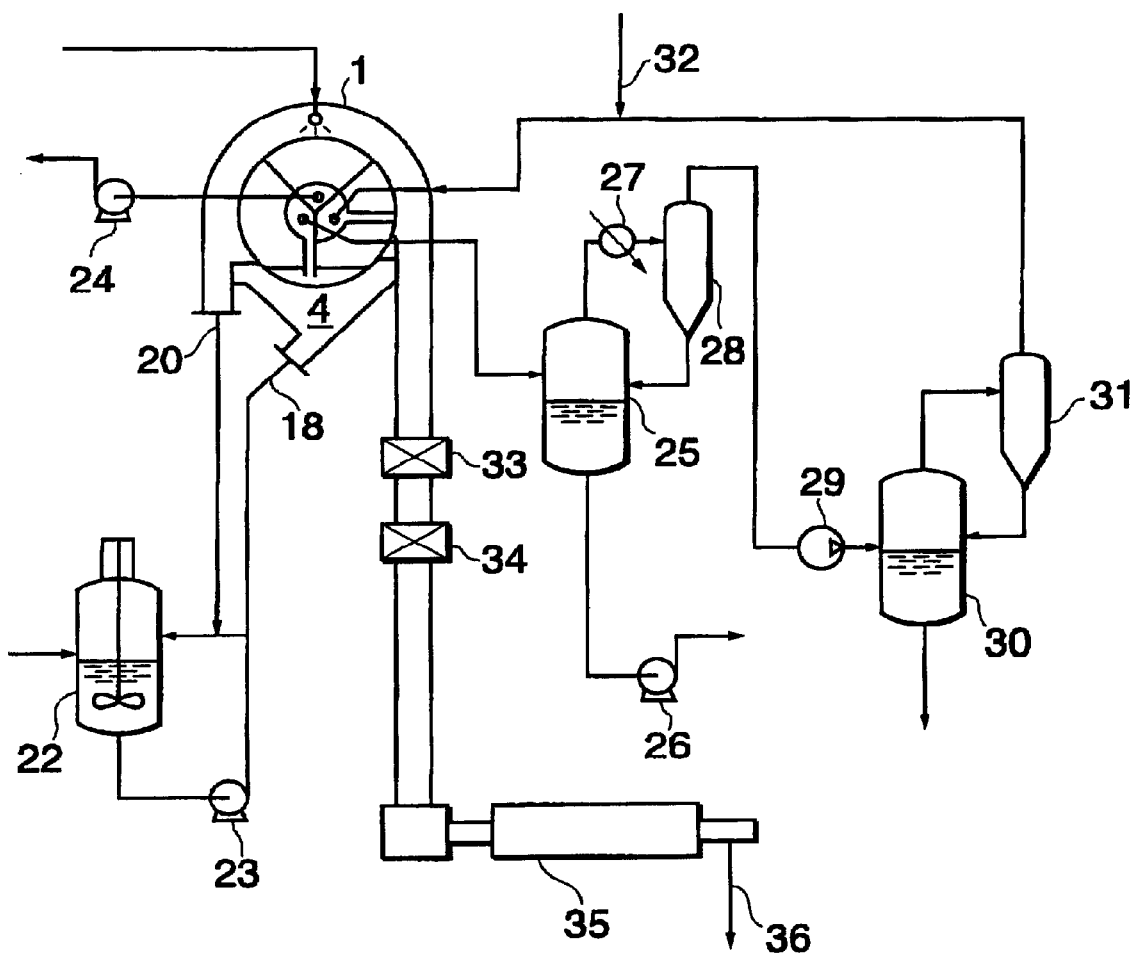
FIG. 2 shows a flow diagram exhibiting a process for recovering crystals as a preferred embodiment of the present invention.

In the flow chart shown in FIG. 2, a slurry to be treated is supplied to the portion for supplying a slurry 18 of RVF 1 by a pump 23 via a tank for a slurry 22, discharged from the portion for circulating a slurry 20 and circulated. A washing liquid in the portion for collecting a liquid 13 is discharged to the outside of the system by a pump 24.

The filtrate and the blowing gas from the portion for suction 8 in FIG. 1 is transferred to a tank for a filtrate 25 and the filtrate is discharged to the outside of the system by a pump 26. At an upper portion of the tank for a filtrate 25, a cooler 27 is disposed. The cooled gas is separated from mist by a mist separator 28 and then discharged by a vacuum pump 29. At the outlet of the vacuum pump 29, a separator sealed with a liquid 30 and a mist separator 31 are disposed and the gas discharged by the vacuum pump 29 is used as the blowing gas in RVF.

The cake cleaved in RVF 1 is taken out from the portion for taking out a cake 21 shown in FIG. 1 via a shutter 33 and a shutter 34, dried by a drier 35 and recovered as crystals (a product) at an outlet for a product 36.

In the process for recovering the crystals, the slurry kept in the tank for a slurry 22 is supplied to a bottom portion of RVF 1 by the pump 23 and filtration under suction, washing, filtration under suction and cleavage (blowing) are successively conducted while the filter medium is rotated. The procedures will be described more specifically in the following.

The pressure at the inside of the rotating drum is made lower than the outside by the working of the vacuum pump 29 via the portion for suction 8. As the result, the slurry supplied at the bottom portion of RVF 1 is filtered through the rotating filter medium 3. The crystals in the slurry 4 is caught by the filter medium 3, form a cake 9 and move upwards. A portion of the slurry 4 overflows the dam 19 and is recycled to the tank for a slurry 22 via the portion for circulating a slurry 20.

The cake 9 is washed with a washing liquid sprayed from the pipes for a washing liquid 10 in the area for washing 11, separated from the washing liquid in the area for removing a liquid 12 and move downwards. In the area for cleavage 16, a blowing gas is supplied to the pipe for supplying a blowing gas 17 and blown through the filter medium in the portion for blowing 14 and the cake 9 is cleaved. The filter medium 3 from which the cake 9 has been cleaved further moves downwards and reaches the filtering area 5 again.

The filtrate 6 and the blowing gas 7 sucked at the portion for suction 8 is transferred to the tank for a filtrate 25 and the filtrate 6 is discharged to the outside of the system by the pump 26.

The cake 9 cleaved in the area for cleavage 16 is taken out from the outlet for a cake 21 via the shutter 33 and the shutter 34, dried by the drier 35 and recovered as crystals (a product) at the outlet for a product 36.

The major point of the present invention is to connect a line for supplying the vapor of a solvent 32 to the line of the blowing gas coming out of the mist separator 31 and to supply a vapor having the same composition as that of the solvent. When the mother liquor of the slurry 4 is water, the vapor having the same composition as that of the solvent naturally means steam. When the mother liquor of the slurry 4 is acetic acid containing water, the vapor of acetic acid containing steam in an amount such that the composition is close to that of the mother liquor is suitable as the vapor having the same composition as that of the solvent. However, steam or the vapor of acetic acid may also be used.

In an ordinary apparatus for producing terephthalic acid, one or more crystallizing tanks are disposed at the upstream of the tank for a slurry 22. In the crystallization tank, the temperature of the slurry is lowered by flash vaporization. It is advantageous that the vapor formed by the flash vaporization is supplied via the line for supplying the vapor of a solvent 32.

By supplying the vapor having the same composition as that of the solvent via the line for supplying the vapor of a solvent 32, as the result, clogging of the filter medium can be prevented and the continuous operation can be conducted for a long period of time. Although the reason for this advantageous result is not fully understood, the result is considered to be obtained due to a combination of the following effects.

As the first effect, the volume of the blowing gas can be increased by supplying the vapor having the same composition as that of the solvent. As the result, it is expected that the cleavage of the crystals in the area for cleavage 16 can be performed completely. Since the vapor of the solvent supplied via the line for supplying the vapor of a solvent 32 is transferred to the tank for a filtrate 25 via the portion for suction 8 after being used as the blowing gas, an advantageous result is obtained in that the amount of the gas treated by the vacuum pump 29 is little affected by the increase in the volume of the blowing gas due to the supply of the vapor having the same composition as that of the solvent.

As the second effect, wetness of the blowing gas is increased by supplying the vapor of the solvent. As the result, it is expected that the phenomenon of the crystals to stuck to the filter medium may be suppressed. Moreover, it is expected that mist of the solvent remaining in the blowing gas in a small amount can remove residual fine crystals attached to the filter medium.

As the third effect, the temperature of the blowing gas is elevated by supplying the vapor having the same composition as that of the solvent. More complete cleavage can be expected due to the elevated temperature of the blowing gas.

As will be shown by the examples later, the content of wetness component in the crystals in the portion for taking out crystals 21 decreased as the result of mixing a vapor having the same composition as that of the solvent into the blowing gas. This is an effect unexpected in advance.

Since the vapor of the solvent supplied via the line for supplying the vapor of a solvent 32 is transferred to the tank for a filtrate 25 via the portion for suction 8 after being used as the blowing gas, the amount of gas treated by the vacuum pump 29 is little affected by the increase in the volume of the blowing gas due to the supply of the vapor having the same composition as that of the solvent.

Mist might be formed due to a decrease in the temperature after the mixing with the vapor having the same composition as that of the solvent and before reaching the blowing portion 14. However, no problems were found in actual operations for a long period of time. The decrease in the temperature of the vapor of the solvent can be suppressed by heat insulation of the line leading to RVF.

As described above, the process of the present invention can be advantageously applied to recovery of crystals of crude terephthalic acid and purified terephthalic acid. The process can also be applied to recovery of crystals in a slurry in the processes for producing aromatic carboxylic acids such as isophthalic acid and naphthalenedicarboxylic acid by oxidation of aromatic hydrocarbons with molecular oxygen in solvents containing catalyst components under conditions of a high temperature and a high pressure.

As will be shown with reference to examples in the following, in accordance with the process of the present invention, clogging of a filter medium can be prevented and crystals can be efficiently recovered from a slurry continuously for a long period of time by supplying a vapor having the same composition as that of the solvent as the blowing gas for cleaving a cake.

Since the vapor having the same composition as that of the solvent supplied in the present invention is transferred to the tank for a filtrate via the portion for suction after being used as the blowing gas for cleaving the cake, the vapor can be recycled as the solvent and the increase in the volume of the blowing gas shows no effects on the amount of the gas treated by the vacuum pump. Moreover, the quality of the recovered crystals is improved by the increase in the volume of the blowing gas.

The process for recovering crystals from a slurry of the present invention can be applied to many processes such as the processes for producing aromatic carboxylic acids in accordance with the liquid phase oxidation.

EXAMPLES

The present invention will be described more specifically with reference to examples in the following. However, the present invention is not limited to the examples.

Example 1

A slurry of terephthalic acid in acetic acid containing water (the content of terephthalic acid: 32% by weight; the temperature: 89° C.) which was obtained from an apparatus for commercial production of crude terephthalic acid by oxidation of para-xylene with the air in the presence of a catalyst comprising cobalt, manganese and bromine was treated in accordance with the process shown in FIGS. 1 and 2 and crude terephthalic acid was recovered. Nitrogen gas was used as the blowing gas and a flash vapor (a mixture of the vapor of acetic acid and steam) generated in a tank for crystallization by flash vaporization which was disposed at the upstream of the tank for a slurry 22 was supplied at a rate of 780 kg/hour via the line for supplying the vapor of a solvent 32. The period of time before the filter medium 3 was clogged was 310 hours. The cake taken out from the outlet for a cake 21 was dried at 110° C. for 4 hours and the decrease in the weight by drying was 9.8%.

Comparative Example 1

The same procedures as those conducted in Example 1 was conducted except that the supply of the flash vapor via the line for supplying the vapor of a solvent 32 was not conducted, i.e., nitrogen gas alone was used as the blowing gas. As the result, the period of time before the filter medium 3 was clogged was 24 hours. The cake taken out from the outlet for a cake 21 was dried at 110° C. for 4 hours and the decrease in the weight by drying was 11.3%.

Example 2

A slurry of isophthalic acid in acetic acid containing water (the content of isophthalic acid: 30% by weight; the temperature: 85° C.) which was obtained from an apparatus for commercial production of crude isophthalic acid by oxidation of meta-xylene with the air in the presence of a catalyst comprising cobalt, manganese and bromine was treated in accordance with the process shown in FIGS. 1 and 2 and crude isophthalic acid was recovered. Nitrogen gas was used as the blowing gas and a flash vapor (a mixture of the vapor of acetic acid and steam) generated in a tank for crystallization by flash vaporization which was disposed at the upstream of the tank for a slurry 22 was supplied at a rate of 200 kg/hour via the line for supplying the vapor of a solvent 32. The period of time before the filter medium 3 was clogged was 230 hours. The cake taken out from the outlet for a cake 21 was dried at 110° C. for 4 hours and the decrease in the weight by drying was 10.4%.

Comparative Example 2

The same procedures as those conducted in Example 2 was conducted except that the supply of the flash vapor via the line for supplying the vapor of a solvent 32 was not conducted, i.e., nitrogen gas alone was used as the blowing gas. As the result, the period of time before the filter medium 3 was clogged was 18 hours. The cake taken out from the outlet for a cake 21 was dried at 110° C. for 4 hours and the decrease in the weight by drying was 12.1%.

What is claimed is:

1. A process for recovering crystals from a slurry which comprises supplying a slurry comprising crystals and a solvent to a rotary vacuum filter and successively conducting filtration under suction, washing, filtration under suction and cleavage of a cake continuously by rotation of a cylindrical filter medium, wherein a vapor having a same composition as that of the solvent is supplied as a blowing gas for cleaving the cake.

2. A process for recovering crystals from a slurry according to claim 1, wherein a chemical reaction is conducted under an elevated pressure using the solvent and a flash vapor which is obtained from a reaction product liquid under a reduced pressure and has a same composition as that of the solvent is supplied as the blowing gas for cleaving the cake.

3. A process for recovering crystals from a slurry according to claim 1, wherein, in a process for producing an aromatic carboxylic acid by oxidation of an aromatic hydrocarbon with molecular oxygen in a solvent containing catalyst components under a condition of a high temperature and a high pressure, a slurry comprising crystals of the aromatic carboxylic acid and the solvent is formed after a crystallization step comprising lowering a temperature of a reaction product liquid and the crystals of the aromatic carboxylic acid in the slurry are separated by using a rotary vacuum filter, wherein a vapor having a same composition as that of the solvent is supplied as the blowing gas for cleaving the cake.

4. A process for recovering crystals from a slurry according to claim 3, wherein, in a process comprising oxidizing para-xylene with molecular oxygen in a solvent containing catalyst components, acetic acid containing water is used as the solvent for the oxidation, and crystals of crude terephthalic acid are recovered by supplying a flash vapor, which is obtained by reducing a pressure of an oxidation liquid and is a mixture of a vapor of acetic acid and steam, as the blowing gas for the rotary vacuum filter.

* * * * *